United States Patent [19]

Dettbarn et al.

[11] 4,396,384

[45] Aug. 2, 1983

[54] NEEDLE-LESS INJECTION INSTRUMENT

[75] Inventors: Hans-Jürgen Dettbarn, Marburg; Josef Zimmermann, Sulzbach, both of Fed. Rep. of Germany

[73] Assignee: Hoechst Aktiengesellschaft, Frankfurt am Main, Fed. Rep. of Germany

[21] Appl. No.: 368,156

[22] Filed: Apr. 14, 1982

[30] Foreign Application Priority Data

Apr. 16, 1981 [DE] Fed. Rep. of Germany ....... 3115376

[51] Int. Cl.³ .............................................. A61M 5/30
[52] U.S. Cl. .................................................... 604/68
[58] Field of Search ...................... 604/68, 70, 71, 72, 604/131, 140, 148, 149, 150, 181

[56] References Cited

U.S. PATENT DOCUMENTS

| 2,642,062 | 6/1953 | May ....................................... 604/68 |
| 3,908,651 | 9/1975 | Fudge ................................... 604/71 |
| 4,059,107 | 11/1977 | Iriguchi et al. ....................... 604/71 |
| 4,301,795 | 11/1981 | Zimmerman ........................... 604/70 |

Primary Examiner—John D. Yasko
Attorney, Agent, or Firm—Curtis, Morris & Safford

[57] ABSTRACT

In this injection instrument, the piston pump (A) is connected to a drive motor (B), of which the working piston (5) supported on a working spring (2) is arranged displaceably in a cylindrical bore (6) of the motor housing (1). A pressure chamber (7) which has supply devices (3, 8) and discharge devices (4, 9) for pressure medium is formed in the bore (6).

To ensure that the pressure medium cannot be simultaneously supplied to and discharged from the pressure chamber (7), there is a control shaft (37) which is assigned to valves (8 and 9). The control shaft (37) is provided with a lever (38) and has segment-like recesses (39, 40) which interrupt the engagement of the valves (8, 9) with the control shaft (37). The recesses (39, 40) are arranged on the control shaft (37) so that the valves are not engaged simultaneously with the control shaft (37).

2 Claims, 4 Drawing Figures

NEEDLE-LESS INJECTION INSTRUMENT

The invention relates to a needle-less injection instrument with a piston pump for the medium to be injected, which is connected to a drive motor, of which the working piston, supported on a working spring, is arranged displaceably in a cylindrical bore of the motor housing, a pressure chamber for receiving a pressure medium to tension the working spring being formed in the cylindrical bore, and an inlet valve being located in the supply line for the pressure medium and an outlet valve being located in the discharge line.

Injection instruments of the type mentioned are known from German Auslegeschrift No. 1,213,958. The spring of the drive motor is tensioned hydraulically. The hydraulic chamber of the drive motor is connected by by-pass to a hydraulic-fluid circuit in which a by-pass valve is located. To tension the spring, the latter must be closed by operating a pusher so that the hydraulic fluid can penetrate into the hydraulic chamber. To maintain the pressure, a globe control valve is necessary in the by-pass line. To relax the working spring, a second control valve must be kept open by operating a second pusher, as a result of which the way is opened for the fluid under pressure in the hydraulic chamber to return to the supply vessel for the hydraulic fluid. A disadvantage of this is that the two pushers cn be actuated at the same time. Filling of the hydraulic chamber is therefore not necessarily guaranteed, with the result that incorrect dosages of the medium to be injected cannot be excluded.

The invention is intended to remedy this. The invention, as defined in the claims, achieves the object by an arrangement wherein a control shaft connected to a lever is assigned to the valves, the control shaft having segment-like recesses which interrupt the engagement of the valves with the control shaft and are so arranged relative to the valves that the valves are not engaged simultaneously with the control shaft.

Rams connected to an operating element can be assigned to the lever to operate it.

The advantages achieved by means of the invention are to be seen essentially in the fact that, as a result of the control shaft common to the valves, incorrect operations for supplying pressure medium into the pressure chamber of the working motor and for discharging it therefrom are prevented.

The invention is explained in more detail below with reference to drawings which illustrate only one form of construction and in which.

Figure 1:
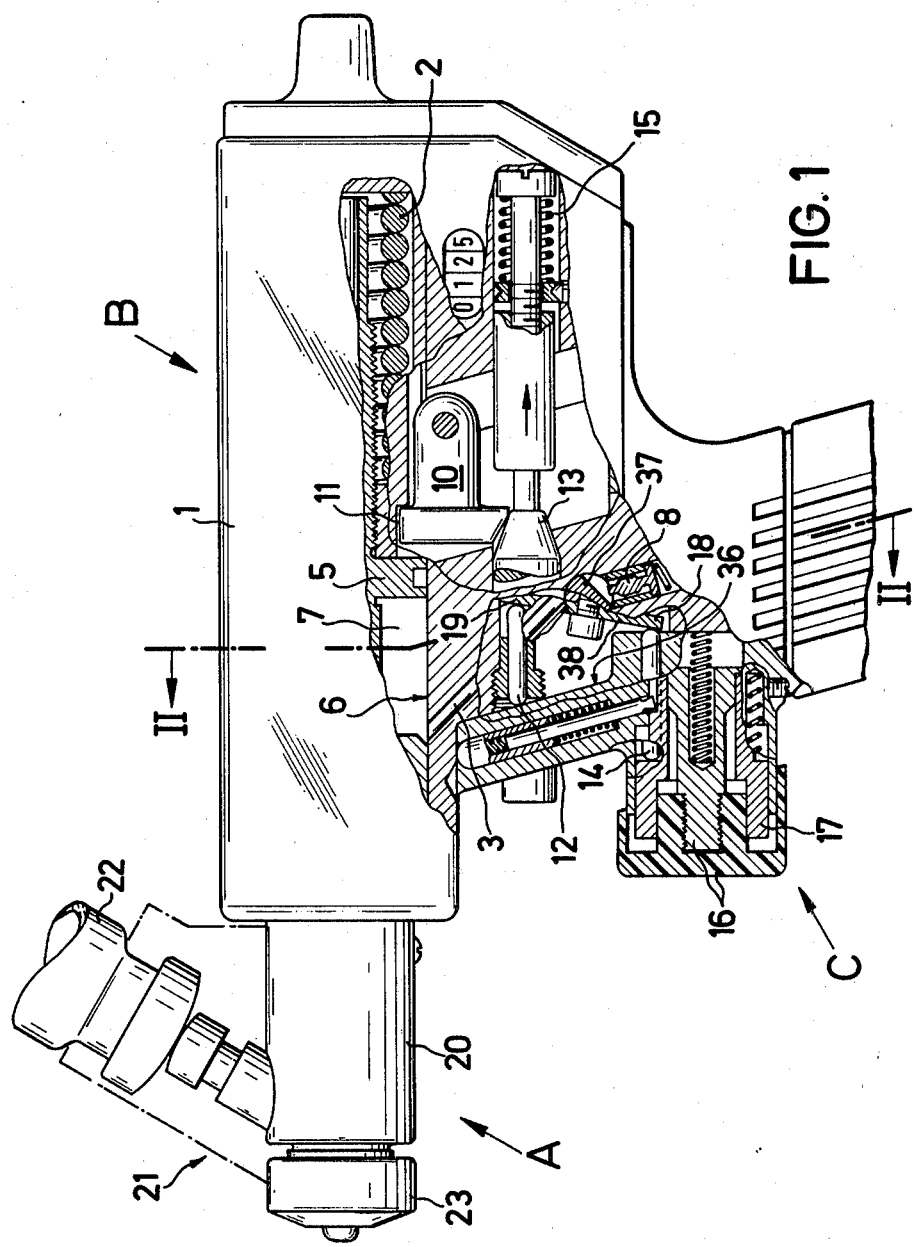
FIG. 1 shows a side view of the injection instrument, partially in section and in sections along various planes, in the cocked state.
Figure 2:
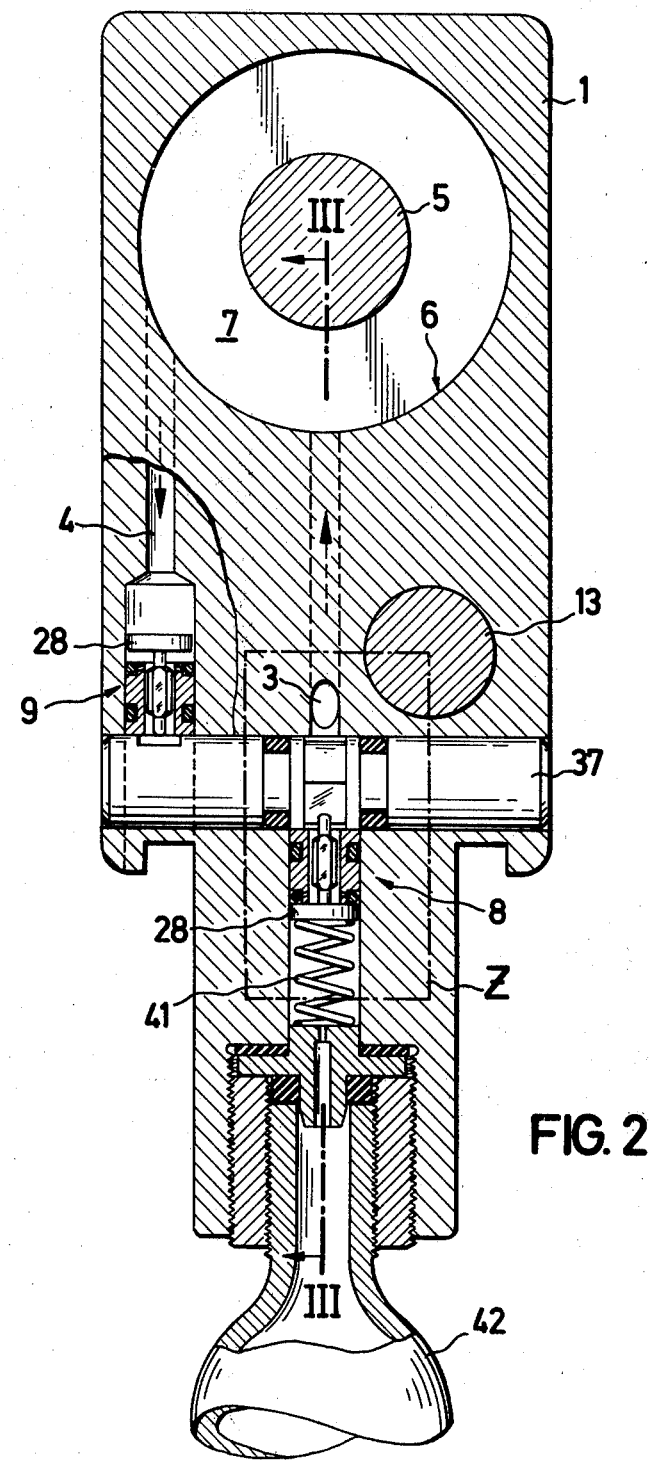
FIG. 2 shows the section II—II of FIG. 1.
Figure 3:
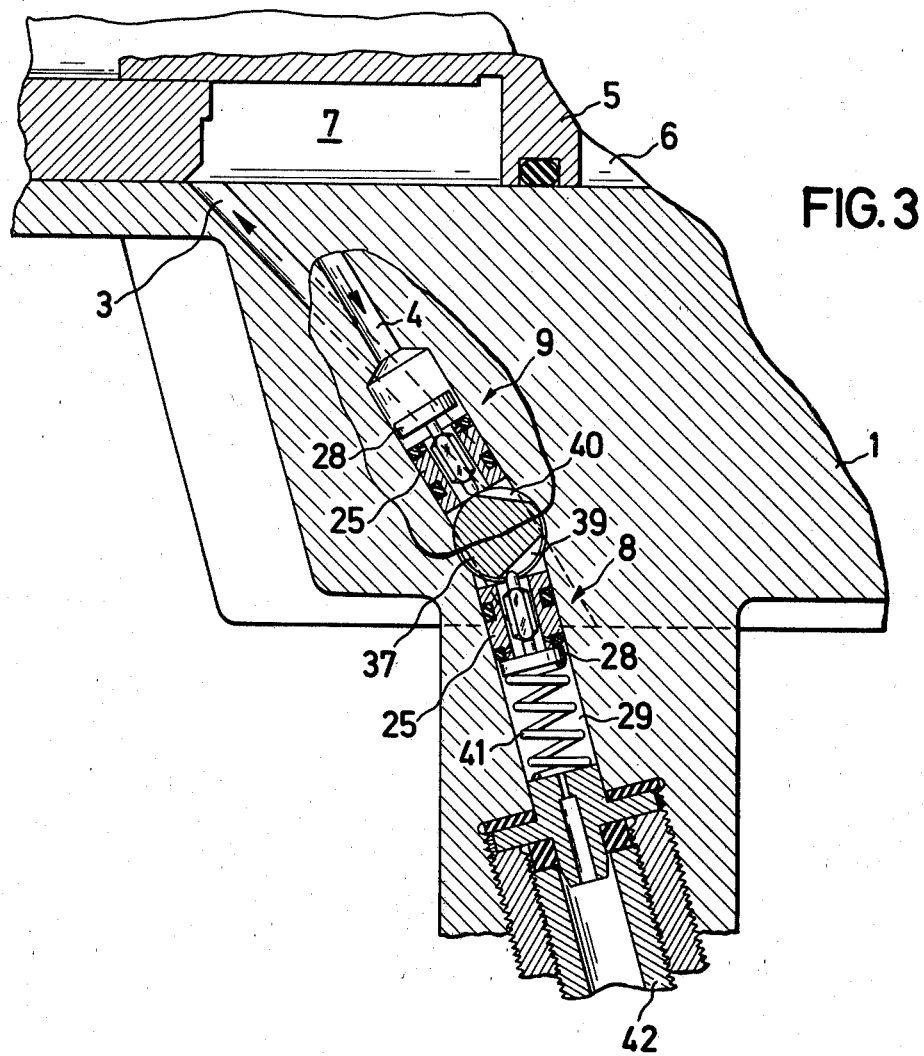
FIG. 3 shows the section III—III of FIG. 2.
Figure 4:
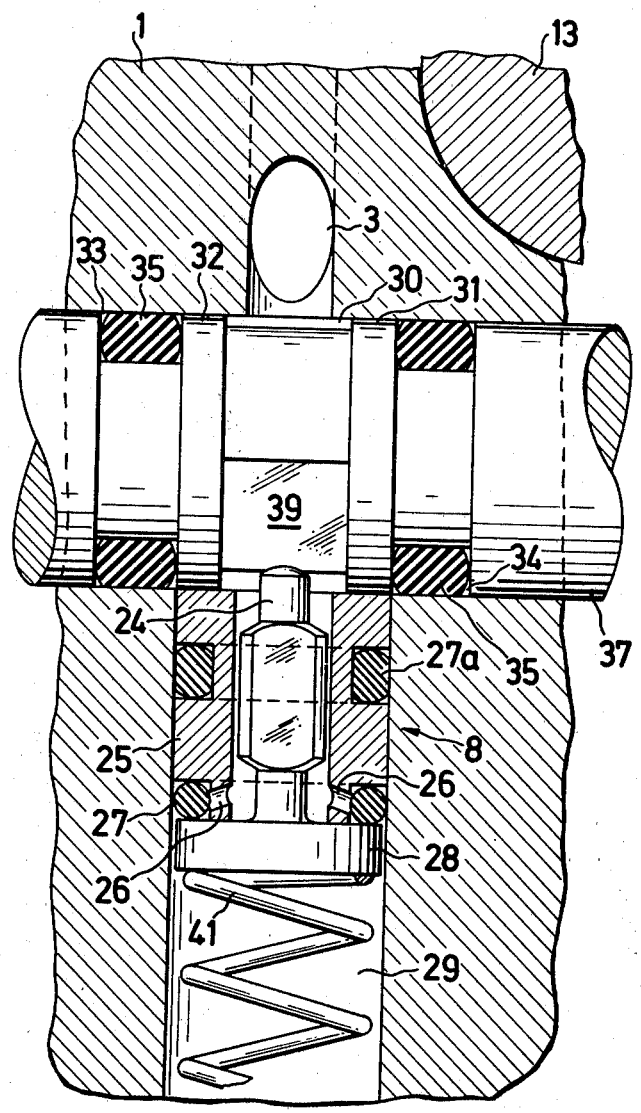
FIG. 4 shows the detail "Z" of FIG. 2.

The needle-less injection instrument consists essentially of a piston pump A for the medium to be injected, which is connected to a drive motor B. The housing (20) of the piston pump A carries a device (21) for receiving a vessel (22) for the medium to be injected. The working piston (5) of the drive motor B is arranged displaceably in a cylindrical bore (6) of the motor housing (1). The working spring (2) of the working piston (5) is tensioned by means of a pressure medium, for example hydraulic fluid or gas, which is supplied via an inlet valve (8) and via a channel (3) to the pressure chamber (7) in the cylindrical bore (6). The pressure medium is discharged from the pressure chamber (7) via a channel (4) and an outlet valve (9). A control shaft (37) provided with a lever (38) is assigned to the inlet valve (8) and outlet valve (9). The control shaft (37) has segment-like recesses (39) and (40) which interrupt the engagement of the valves (8) and (9) with the control shaft (37). The recesses (39) and (40) are arranged on the control shaft (37) so that the valves (8) and (9) cannot engage simultaneously with the control shaft (37). To actuate the lever (38), rams (12) and (14) connected to the operating element C can be assigned to this lever.

The operating element (C) contains, among other things, an operating knob (16) and a sleeve (17). to cock the instrument, the operating knob (16) is pressed, as a result of which the sleeve (17) presses on a ram (14) which, in turn, presses on the lower end (18) of a lever (38) connected firmly to the control shaft (37) and thereby causes a pivoting movement of the control shaft (37). The control shaft (37) opens and closes the inlet valve (8) or the outlet valve (9) respectively. The inlet valve (8) and the outlet valve (9) each consist of a valve disk (28) with guide pins (24) and a bush (25) with gaskets (27, 27a). The bush (25) is located in a bore (29) in the motor housing (1). The control shaft (37) has, in the region of the segment-like recess (39), a grooved portion (30) as a distributor channel for the pressure medium, and, on the right and left, separated by two narrow shoulders (31) and (32), two further grooved portions (33) and (34) for receiving gaskets (35). The bush (25) is supported on the shoulders (31) and (32). When the valve (8) is open, the guide pin (24) rests on the cylindrical grooved portion (30) of the control shaft (37). When the valve (8) is closed, the valve disk (28) rests on the gasket (27), and the guide pin (24) does not touch the control shaft (37) because of the recess (39). The bores (26) are provided for the purpose of pressure compensation, so that, when the valve disk (28) is lifted off, the gasket (27) does not change its position. The outlet valve (9) is of corresponding design.

By pressing on the end (18) of the lever (38), the control shaft (37) pivots, the inlet valve (8) opens and the outlet valve (9) closes. As a result of the flow of pressure medium via the channel (3) into the pressure chamber (7), the working spring (2) is tensioned via the working piston (5). As soon as the pawl (10) engages into the recess (11), the bolt (13), together with the operating element (c) fastened thereto, is drawn in the direction of the arrow by the force of the spring (15). During this time, the face (36) of the operating element (C) presses the ram (12) against the upper end (19) of the lever (38), the latter pivoting the control shaft (37) back into its initial position again. As a result, the inlet valve (8) can be held and closed by the spring (41), and the outlet valve (9) is opened, so that the pressure medium can escape from the pressure chamber (7) via the channel (4). The injection shot is released by pressing the nozzle (23) onto the subject to be injected. (42) denotes a pressure-gas bottle.

We claim:

1. A needle-less injection instrument with a piston pump for the medium to be injected, which is connected to a drive motor, of which the working piston, supported on a working spring, is arranged displaceably in a cylindrical bore of the motor housing, a pressure chamber for receiving a pressure medium to tension the working spring being formed in the cylindrical bore, and an inlet valve being located in the supply line for the pressure medium and an outlet valve being located in the discharge line, wherein a control shaft (37) provided with a lever (38) is assigned to the valves (8, 9), the control shaft (37) having segment-like recesses (39, 40) which interrupt the engagement of the valves (8, 9) with the control shaft (37) and are so arranged relative to the valves that the valves are not engaged simultaneously with the control shaft (37).

2. The needle-less injection instrument as claimed in claim 1, wherein rams (12, 14) connected to an operating element (C) are assigned to the lever (38).

* * * * *